(12) United States Patent
Druma et al.

(10) Patent No.: US 11,006,993 B2
(45) Date of Patent: May 18, 2021

(54) RETRACTABLE INFLATABLE BONE TAMP

(71) Applicant: Medtronic Holding Company Sàrl, Tolochenaz (CH)

(72) Inventors: Calin Druma, San Jose, CA (US); Bruce Chabansky, Palo Alto, CA (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 441 days.

(21) Appl. No.: 15/095,667

(22) Filed: Apr. 11, 2016

(65) Prior Publication Data

US 2016/0220293 A1 Aug. 4, 2016

Related U.S. Application Data

(63) Continuation of application No. 13/082,770, filed on Apr. 8, 2011, now abandoned.

(51) Int. Cl.
*A61B 17/56* (2006.01)
*A61M 25/10* (2013.01)
*A61B 17/88* (2006.01)
*A61M 25/01* (2006.01)

(52) U.S. Cl.
CPC ...... *A61B 17/8855* (2013.01); *A61B 17/8805* (2013.01); *A61M 25/0119* (2013.01)

(58) Field of Classification Search
CPC .......... A61B 17/8805; A61B 17/8855; A61M 25/0119; A61M 25/0113; A61M 25/09041; A61F 2/95–2/97; A61F 2/2427–2/2439
See application file for complete search history.

(56) References Cited

U.S. PATENT DOCUMENTS

| | | | |
|---|---|---|---|
| 1,087,845 A | 2/1914 | Stevens | |
| 3,168,092 A | 2/1965 | Silverman | |
| 3,835,854 A | 9/1974 | Jewett | |
| 4,271,839 A * | 6/1981 | Fogarty | A61M 25/0119 604/271 |
| 4,383,532 A * | 5/1983 | Dickhudt | A61N 1/0551 607/117 |
| 4,526,175 A | 7/1985 | Chin et al. | |
| 4,637,404 A | 1/1987 | Gessman | |
| 4,946,440 A | 8/1990 | Hall | |
| 4,998,923 A * | 3/1991 | Samson | A61M 25/104 604/913 |

(Continued)

FOREIGN PATENT DOCUMENTS

JP WO 2010110043 A1 * 9/2010 ......... A61B 1/00082

*Primary Examiner* — Kathleen S Holwerda
(74) *Attorney, Agent, or Firm* — Sorell, Lenna & Schmidt, LLP

(57) ABSTRACT

An inflatable bone tamp for performing a minimally invasive surgical procedure includes an outer shaft defining an internal lumen, an inflatable structure coupled to the outer shaft, and an inner shaft movably disposed within the internal lumen and coupled to a distal end region of the inflatable structure. The internal lumen is sized to receive the inflatable structure, such that by moving the inner shaft relative to the outer shaft, the inflatable structure can be retracted into the internal lumen (and likewise can be extended from within the internal lumen for deployment in bone). This retraction capability can beneficially protect the inflatable structure during positioning/removal, and can also enhance recovery from radial tears of the inflatable structure.

19 Claims, 11 Drawing Sheets

(56) References Cited

U.S. PATENT DOCUMENTS

| | | | |
|---|---|---|---|
| 5,015,231 A * | 5/1991 | Keith | A61M 25/1038 604/103 |
| 5,129,402 A | 7/1992 | Koll et al. | |
| 5,209,728 A * | 5/1993 | Kraus | A61M 25/104 604/913 |
| 5,346,498 A * | 9/1994 | Greelis | A61M 25/0119 604/271 |
| 5,383,889 A * | 1/1995 | Warner | A61B 17/00234 604/908 |
| 5,439,445 A | 8/1995 | Kontos | |
| 5,522,833 A | 6/1996 | Stephens et al. | |
| 5,556,376 A | 9/1996 | Yoon | |
| 5,707,376 A * | 1/1998 | Kavteladze | A61F 2/90 623/1.11 |
| 5,868,753 A | 2/1999 | Schatz | |
| 6,071,285 A | 6/2000 | Lashinski et al. | |
| 6,171,234 B1 | 1/2001 | White et al. | |
| 6,280,456 B1 | 8/2001 | Scribner et al. | |
| 6,558,318 B1 | 5/2003 | Daniel et al. | |
| 6,623,451 B2 | 9/2003 | Vigil | |
| 6,719,773 B1 | 4/2004 | Boucher et al. | |
| 7,879,005 B2 | 2/2011 | Wu et al. | |
| 7,892,275 B2 | 2/2011 | Hartley et al. | |
| 8,617,114 B2 * | 12/2013 | Oepen | A61M 25/1006 604/103.02 |
| 8,778,006 B2 | 7/2014 | Fargahi et al. | |
| 2004/0186511 A1 | 9/2004 | Stephens et al. | |
| 2005/0137620 A1 | 6/2005 | Alkhatib | |
| 2006/0149136 A1 | 7/2006 | Seto et al. | |
| 2007/0078386 A1 | 4/2007 | Salazar | |
| 2008/0140107 A1 | 6/2008 | Bei et al. | |
| 2008/0262296 A1 * | 10/2008 | Suzuki | A61B 1/00133 600/106 |
| 2009/0254063 A1 * | 10/2009 | Oepen | A61M 25/1006 604/509 |
| 2009/0281619 A1 | 11/2009 | Le et al. | |
| 2009/0287203 A1 | 11/2009 | Mazzone et al. | |
| 2010/0094310 A1 | 4/2010 | Warring et al. | |
| 2010/0106236 A1 | 4/2010 | Nelson | |
| 2010/0234838 A1 | 9/2010 | Watson | |
| 2010/0234876 A1 | 9/2010 | Watson | |
| 2010/0286720 A1 | 11/2010 | Shaked et al. | |
| 2012/0041261 A1 * | 2/2012 | Shunsuke | A61B 1/00082 600/115 |

* cited by examiner

RETRACTABLE INFLATABLE BONE TAMP

This application is a continuation of U.S. patent application Ser. No. 13/082,770, filed on Apr. 8, 2011, which is expressly incorporated herein by reference, in its entirety.

FIELD OF THE INVENTION

The invention relates to a system and method for performing a surgical procedure, and in particular, to an inflatable device that incorporates a retractable inflation structure.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Because patients with these problems are typically older, and often suffer from various other significant health complications, many of these individuals are unable to tolerate invasive surgery. Therefore, in an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

Conventional inflatable bone tamps (IBTs) used in kyphoplasty procedures incorporate a "dual lumen" construction, in which a balloon is connected between distal tips of coaxial catheters. The catheters are fixed relative to one another, such that the length of the balloon is substantially defined by the extension of the distal end of the inner catheter beyond the distal end of the outer catheter. During a typical surgical procedure, a cannula is positioned adjacent to the target bone structure to provide an access path for the inflatable bone tamp, with the balloon being guided through this access path to the target bone structure.

If the balloon suffers a radial tear during inflation (at the target bone structure), subsequent removal of the balloon through the cannula can be difficult. Specifically, the metal edge at the proximal opening of the cannula can catch or snag the unattached end(s) of the torn balloon, thereby preventing removal of the inflatable bone tamp and/or undesirably causing bits of material to separate from the balloon.

Accordingly, it is desirable to provide an IBT that can better protect the inflatable structure and reduce the recovery issues associated with a radial balloon tear.

SUMMARY OF THE INVENTION

By providing an inflatable bone tamp having an inflatable structure coupled between an outer shaft and a movable inner shaft capable of retracting the inflatable structure into the outer shaft, the possibility of catching/snagging the inflatable structure on the cannula can be reduced.

In one embodiment, an inflatable bone tamp can include an elongate outer shaft, an inflatable structure, an inner shaft movably positioned within the outer shaft, and an inflatable structure coupled between the two shafts. The outer shaft defines an internal lumen sized such that by moving the inner shaft relative to the outer shaft, the inflatable structure can be retracted into the internal lumen. In various embodiments, the inflatable bone tamp can include a sealing element to prevent leakage of inflation fluid from within the outer shaft around the internal shaft, such as a Tuohy-Borst connector, a gasket, or an O-ring.

In various embodiments, the proximal end region of the inflatable structure can be coupled to the distal end region of the external shaft, and the distal end region of the inflatable structure can be coupled to the distal end region of the inner shaft. In some embodiments, the inner shaft can include a securing feature (e.g., a shoulder, cap, or cup) at its distal tip to ensure that the distal end of the inflatable structure remains attached to the inner shaft during retraction.

In some embodiments, the inflatable bone tamp can further include a retraction controller for securing (fixing) the position of the inner shaft relative to the outer shaft (e.g., via a ratchet, clamp, or latch, among other mechanisms). In one embodiment, the inner shaft is freely movable with respect to the outer shaft until a stop feature on the inner shaft interfaces with the retraction controller to prevent any further extension (i.e., once a maximum extension of inflatable structure beyond the distal end of the outer shaft is reached, the stop feature engages with the retraction controller to prevent further distal movement of the inner shaft relative to the outer shaft).

In various other embodiments, the retraction controller can further control the positioning of the inner shaft relative to the outer shaft (i.e., as opposed to having the user solely define this relative positioning via direct manipulation of the inner shaft). Such control can be provided using any appropriate adjustment mechanism, such as a pull roller, spur gear, helical gear, worm wheel gear, and rack gear, among others. In various embodiments, the inner shaft can include features for interfacing with such mechanisms (e.g., teeth, slots, notches, or threads, among others).

In another embodiment, a surgical system for treating bone can include one or more inflatable bone tamps incorporating retractable inflatable structures. In various embodiments, the surgical system can include additional equipment for performing a surgical procedure using the inflatable bone tamp(s) (e.g., one or more cannulas sized to accept the inflatable bone tamp(s), access tools such as drills, guide wires, obturators, trocars, and/or curettes) and/or instructions for performing the surgical procedure using the one or more inflatable bone tamps.

In another embodiment, a surgical procedure such as kyphoplasty can be performed by creating an access path (e.g., using a cannula), placing an inflatable bone tamp having a retractable inflatable structure at the target bone (e.g., a fractured vertebra), optionally extending the inflatable structure, inflating the inflatable structure to compact cancellous bone and/or restore cortical bone profile (e.g., restore vertebral body height), deflating the inflatable structure, retracting the inflatable structure into the shaft of the inflatable bone tamp, removing the inflatable bone tamp, and optionally delivering bone filler material (e.g., bone cement or bone graft) into the target bone.

As will be realized by those of skilled in the art, many different embodiments of an inflatable bone tamp exhibiting an outwardly tapering expansion profile, systems, kits, and/or methods of using such an inflatable bone tamp according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By providing an inflatable bone tamp having an inflatable structure coupled between an outer shaft and a movable inner shaft capable of retracting the inflatable structure into the outer shaft, the possibility of catching/snagging the inflatable structure on the cannula can be reduced.

Figure 1A:
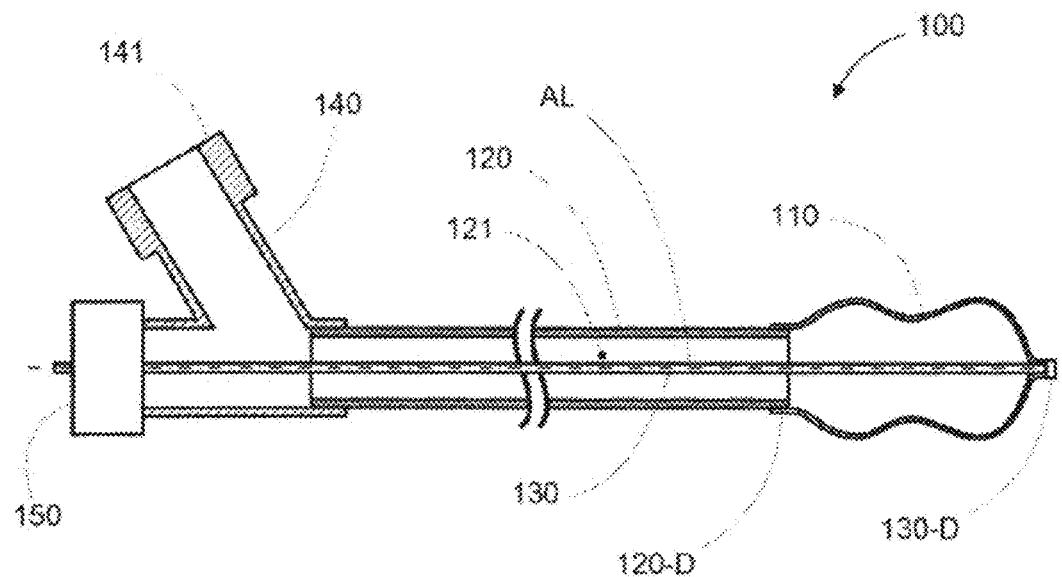
FIGS. 1A-1B show an exemplary inflatable bone tamp that incorporates a retractable inflatable structure.

FIG. 1A shows an embodiment of an inflatable bone tamp 100 that includes an outer shaft 120 (e.g., a catheter), an inflatable structure 110 (e.g., a balloon) at the distal end of shaft 120, a connector 140 (e.g., a Luer Lock fitting) at the proximal end of shaft 120, an inner shaft 130, and a retraction controller 150. Note that while connector 140 is depicted as a "Y" connecter (i.e., two fittings or ports) for exemplary purposes, connector 140 can take any shape and can include any number of fittings.

Inflatable structure 110 can be formed from any type of inflatable material, including non-compliant materials (e.g., many nylon and polyethylene materials), semicompliant materials (e.g., many polyurethane materials), compliant materials (e.g., latex rubber), or any combination thereof. Inflatable structure 110 can also have any size/shape. While a dual-lobed ("peanut shaped") configuration is depicted for exemplary purposes, in various other embodiments, inflatable structure 110 can be ovoid, spheroid, cylindrical, or any other shape. In various other embodiments, inflatable structure, shaft 120, and/or shaft 130 can include radiopaque elements, markings, and/or patterns to facilitate visualization and/or positioning under fluoroscopic imaging.

Note further that shaft 120 can likewise be formed from any material or combination of materials providing sufficient structural support to allow inflatable structure 110 to be inflated within bone. For example, in various embodiments, shaft 120 can be formed from nylon, polyethylene, polyurethane, stainless steel, nitinol, multiple layers of different materials, or any other desired construction and composition.

Shaft 120 defines an inner lumen 121 in which inner shaft 130 is at least partially disposed, and inflatable structure 110 is coupled between a distal end region 120-D of outer shaft 120, and a distal end region 130-D of inner shaft 130. In some embodiments, inflatable structure 110 can be inflated through lumen 121 of shaft 120 (e.g., using inflation fluid delivered via connector 140). In various other embodiments, inner shaft 130 can define its own internal lumen for delivering inflation fluid to inflatable structure 110.

Figure 1B:
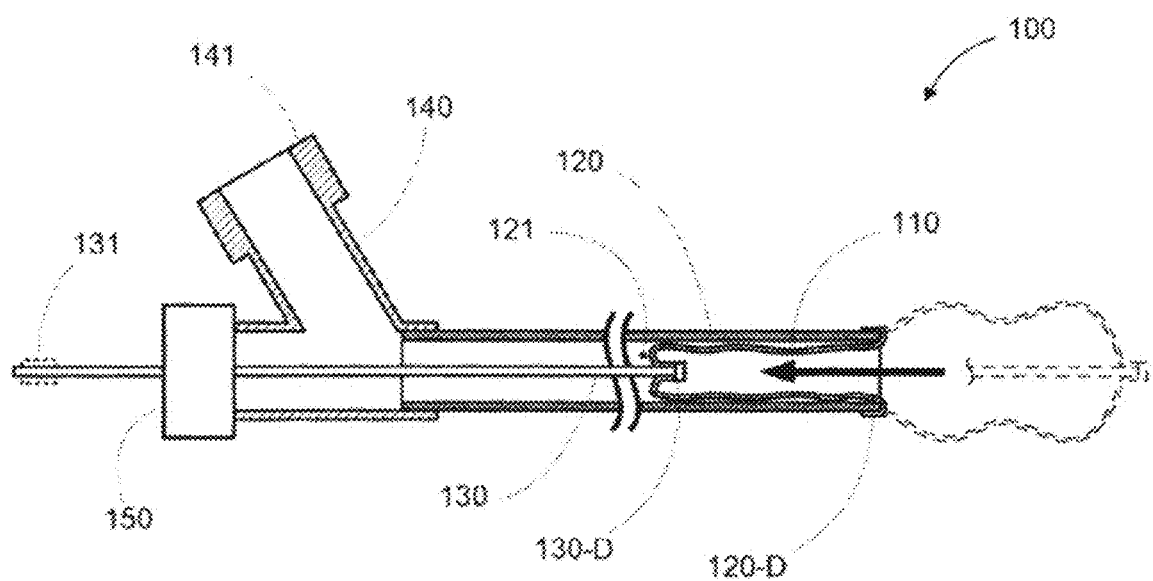

As shown in FIG. 1B, Inner lumen 121 of shaft 120 is further sized such that inflatable structure 110 can be withdrawn into inner lumen 121 by moving inner shaft 130 relative to shaft 120. Retraction controller 150 allows the position of inner shaft 130 relative to shaft 120 to be adjusted and/or set. For example, in some embodiments, retraction controller 150 can simply act as a sealing element that allows for movement of inner shaft 130 along inner lumen 121 without allowing leakage of inflation fluid delivered via connector 140 and/or outer shaft 120 to inflatable structure 110. For example, controller 150 can include an elastomeric gasket, a Tuohy-Borst connector, an o-ring(s) seated in inner shaft 130, or any other mechanism providing leak-resistant relative motion capabilities.

In some embodiments, distal end 130-D of inner shaft 130 can include a shoulder or other feature having a larger diameter than the portion of inner shaft 130 bonded to inflatable structure 110. This raised structure can help to ensure that inflatable structure 110 remains securely attached to inner shaft 130 even as it is pulled into inner lumen 121 of shaft 120.

An optional positioning feature 131 on inner shaft 130 can limit extension of inner shaft distal end 130-D to a predetermined distance beyond outer shaft distal end 120-D (e.g., retraction controller 150 can define a passageway for inner shaft 130 that is sized to prevent passage of positioning feature 131 by abutting retraction controller 150), thereby defining the length of inflatable structure 110 during inflation. When retraction of inflatable structure 110 is desired, inner shaft 130 can simply be manually pulled into lumen 121 (e.g., by gripping inner shaft 130 directly and/or holding optional positioning feature 131).

Figure 2A:
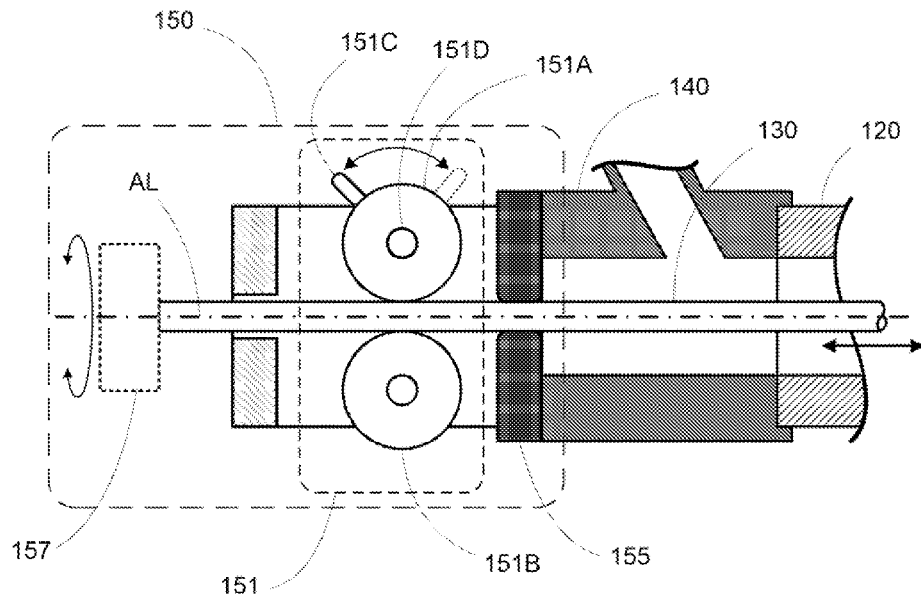
FIGS. 2A-2B show exemplary embodiments of a retraction controller for the inflatable bone tamp of FIGS. 1A-1B.

In various other embodiments, retraction controller 150 can incorporate any mechanism for adjusting and setting the position of inner shaft 130 relative to outer shaft 120. For example, FIG. 2A shows an exemplary embodiment of retraction controller 150 that includes a drive mechanism 151 formed by rotary driver elements 151A and 151B. Rotary driver elements 151A and 151B are engaged with inner shaft 130 such that rotation of driver elements 151A and 151B (e.g., in response to user movement of an optional actuator 151C) adjusts the longitudinal position of inner shaft 130 (i.e., the position of inner shaft 130 relative to outer shaft 120 along longitudinal axis AL). A locking mechanism 151D can then be used to fix the position of inner shaft 130. Locking mechanism 151D can be a ratchet mechanism, a clamp, a releasable latch, or any other mechanism for maintaining the position set by drive mechanism 151.

Note that in some embodiments, locking mechanism 151D can allow inner shaft 130 to be set at specific predetermined positions that correspond to specific configurations for inflatable structure 110 (e.g., a latching mechanism that engages when inner shaft 130 is in either the fully extended (e.g., FIG. 1A) or fully retracted (e.g., FIG. 1B) positions). In other embodiments, locking mechanism 151D can allow for more length variability, either in discrete increments (e.g., a ratchet) or continuously (e.g., a friction fit and/or clamp).

In some embodiments, retraction controller can further include a sealing element 155 that allows for passage, movement, and/or manipulation of inner shaft 130 without allowing leakage of inflation fluid delivered via connector 140 and/or outer shaft 120 to inflatable structure 110 (not shown). For example, as noted above, sealing element 155 can be an elastomeric gasket, a Tuohy-Borst connector, an o-ring(s) seated in inner shaft 130, or any other mechanism providing leak-resistant relative motion capabilities.

Note that in various embodiments, drive mechanism 151 can incorporate a friction drive, such that driver element 151A and/or 151B simply press against inner shaft 130 and rotate to advance/retract inner shaft 130 (e.g., pull rollers). In various other embodiments, driver element 151A and/or 151B can be a gear (e.g., spur gear, helical gear, worm wheel gear, rack gear, etc.) that engages with notches, grooves, threads, or any other features on inner shaft 130.

In various other embodiments, extension drive mechanism 151 can further include an optional rotation controller 157 that rotates inner shaft 130 with respect to outer shaft 120. This can allow inflatable structure 110 to be wrapped around inner shaft 130 to facilitate positioning and/or removal of inflatable bone tamp 100 in confined spaces. Note that while depicted as a simple knob attached to inner shaft 130 for exemplary purposes, various other embodiments will be readily apparent, including having retraction controller 150 itself rotate to rotate inner shaft 130.

In some embodiments, inner shaft 130 can be a generally rigid element that is longitudinally inextensible (e.g., stainless steel or nitinol wire/rod) or minimally longitudinally extensible (e.g., polyurethane or nylon catheter), or a combination of various materials. Typically, such embodiments of inner shaft 130 would be substantially rigid as well, but in some embodiments, inner shaft 130 can be a flexible element.

Figure 2B:
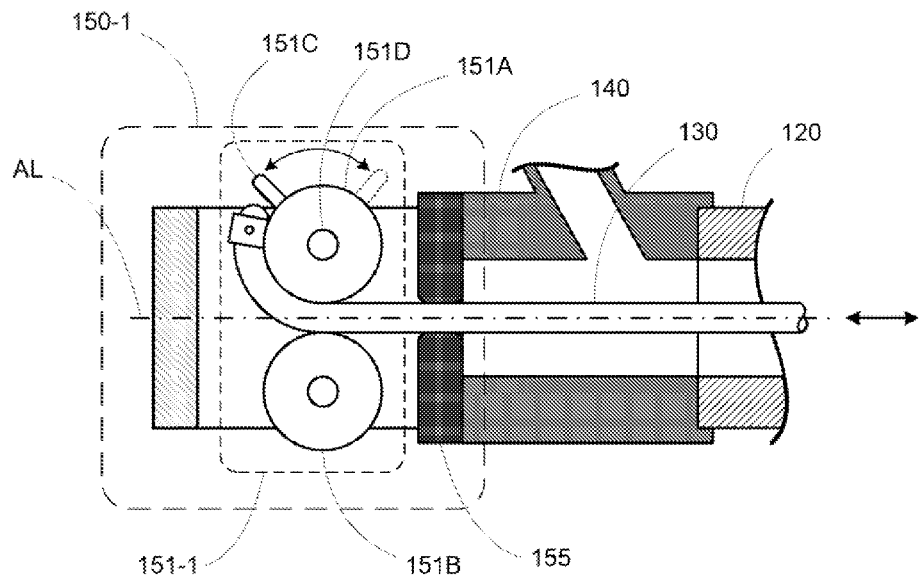

For example, FIG. 2B shows an alternative embodiment of inner shaft 130 that exhibits flexibility while maintaining a desired degree of longitudinal inextensibility (e.g., a push-pull cable or nitinol wire, among others). In FIG. 2B, inner shaft 130 is wrapped/unwrapped around driver element 151A to retract/extend inner shaft 130. Various other embodiments will be readily apparent.

Figure 3:
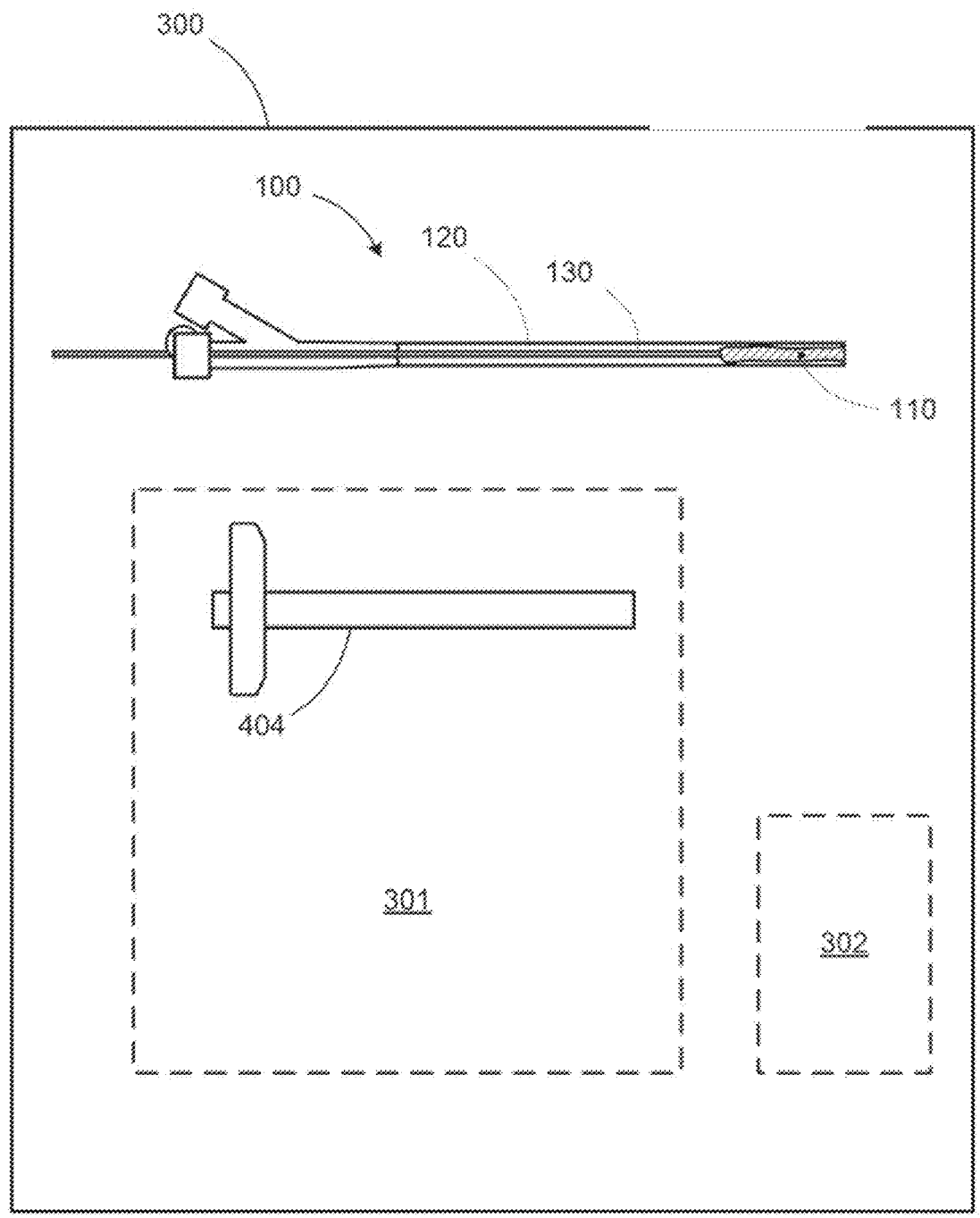
FIG. 3 shows a kit that includes the inflatable bone tamp of FIGS. 1A-1B.

FIG. 3 shows a diagram of a kit 300 for use in performing a surgical procedure (e.g., a kyphoplasty procedure described with respect to FIGS. 4A-4H below). Kit 300 includes an inflatable bone tamp 100 (as described above with respect to FIGS. 1A-1B) that incorporates an outer shaft 120, and an inflatable structure 110 that can be retracted into outer shaft 120 by an inner shaft 130. In various embodiments, kit 300 can further include optional additional instruments 301, such as a cannula 404 sized to receive inflatable bone tamp 100, an introducer, guide pin, drill, curette, and/or access needle, among others (only cannula 404 is shown for clarity). In various other embodiments, kit 300 can further include optional directions for use 302 that provide instructions for using inflatable bone tamp 100 and optional additional instruments 301 (e.g., instructions for performing a kyphoplasty procedure using inflatable bone tamp 100 and optional additional instruments 301).

Figure 4A:
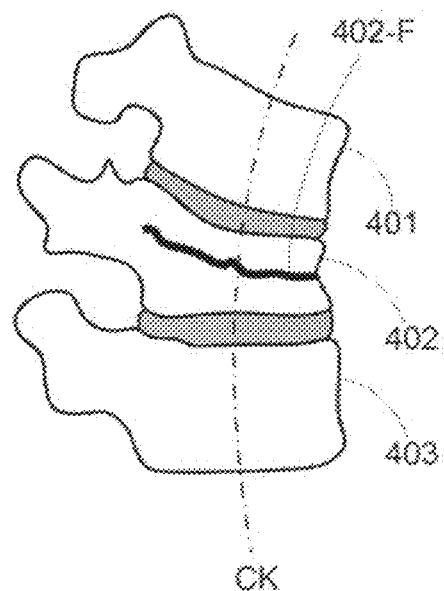
FIGS. 4A-4H show an exemplary kyphoplasty procedure using the inflatable bone tamp of FIGS. 1A-1B.

FIGS. 4A-4H show an exemplary kyphoplasty procedure using an inflatable bone tamp 100 as described with respect to FIGS. 1A-1B above. FIG. 4A shows a portion of a human vertebral column having vertebrae 401, 402, and 403. Vertebra 402 has collapsed due to a vertebral compression fracture (VCF) 402-F that could be the result of osteoporosis, cancer-related weakening of the bone, and/or physical trauma. The abnormal curvature CK of the spine caused by VCF 402-F can lead to severe pain and further fracturing of adjacent vertebral bodies.

Figure 4B:
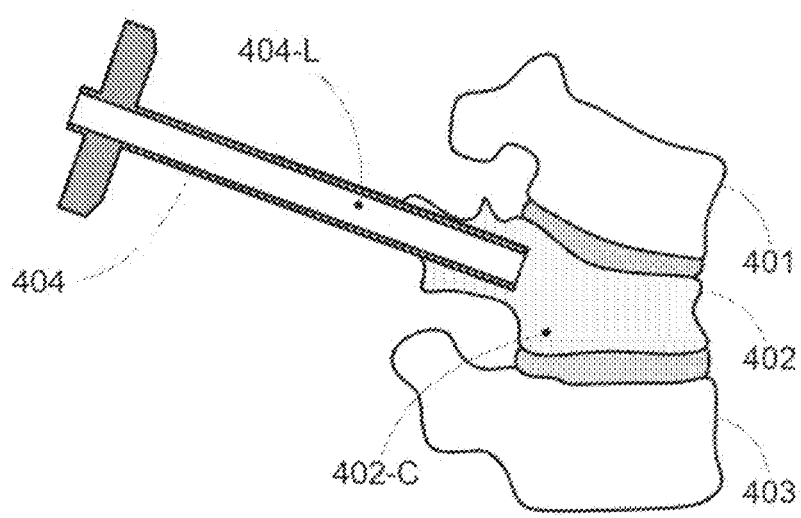

FIG. 4B shows a cannula 404 being positioned next to the target surgical location, which in this case is the cancellous bone structure 402-C within fractured vertebra 402. In this manner, a percutaneous path to vertebra 402 is provided via an interior lumen 404-L of cannula 404. Typically, cannula 404 is docked into the exterior wall of the vertebral body (using either a transpedicular or extrapedicular approach) using a guide needle and/or dissector, after which a drill or other access tool (not shown) is used to create a path further into the cancellous bone 402-C of vertebra 402. However, any other method of cannula placement can be used to position cannula 404.

Figure 4C:
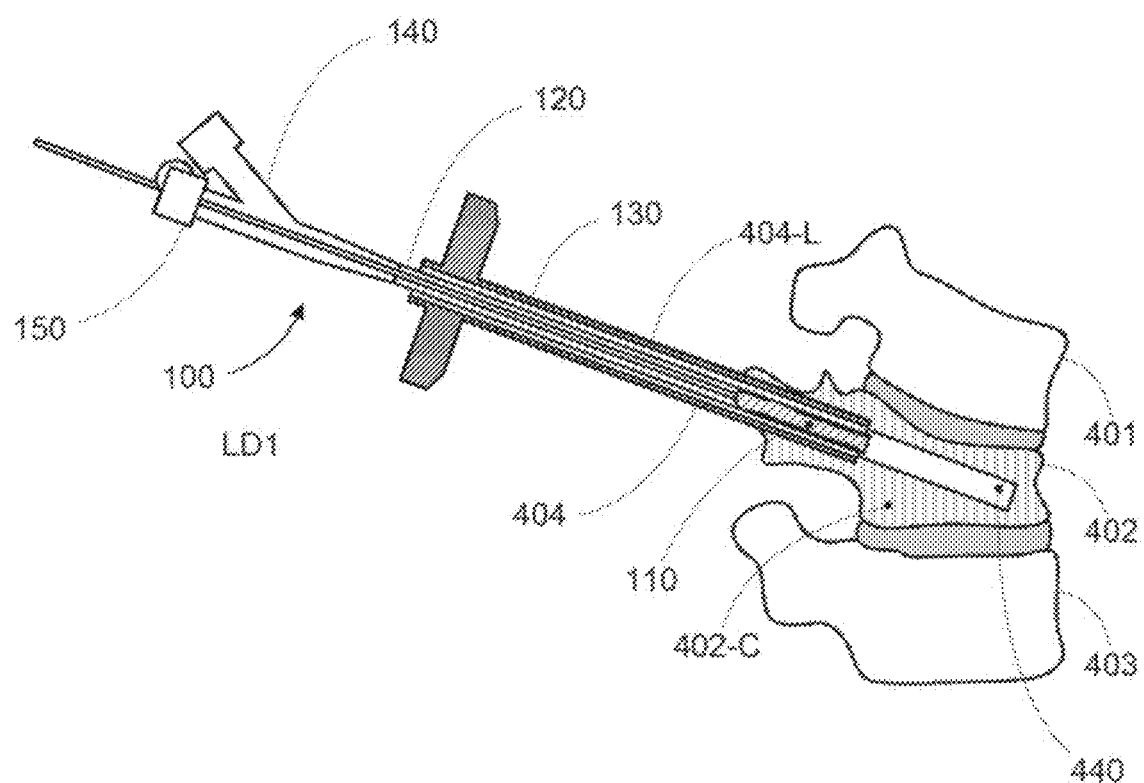

Then in FIG. 4C, an inflatable bone tamp 100 as described above with respect to FIGS. 1A-1B is placed into cannula 404. Inflatable bone tamp 100 includes an outer shaft 120 (e.g., a catheter), an inflatable structure 110 (e.g., a balloon) mounted towards the distal end of shaft 120, an inner shaft 130 disposed at least partially within outer shaft 120, a connector 140 (e.g., a Luer Lock fitting) at the proximal end of shaft 120, and an retraction controller 150 for positioning inner shaft 130 relative to outer shaft 120.

As described above with respect to FIGS. 1A-1B, inflatable structure 110 can be retracted into shaft 120 by inner shaft 130, thereby providing greater protection for inflatable structure during insertion into and/or removal from bone environments. For exemplary purposes, FIG. 4C shows inflatable structure 110 fully retracted into shaft 120 during positioning of inflatable bone tamp 100 within vertebra 402.

Figure 4D:
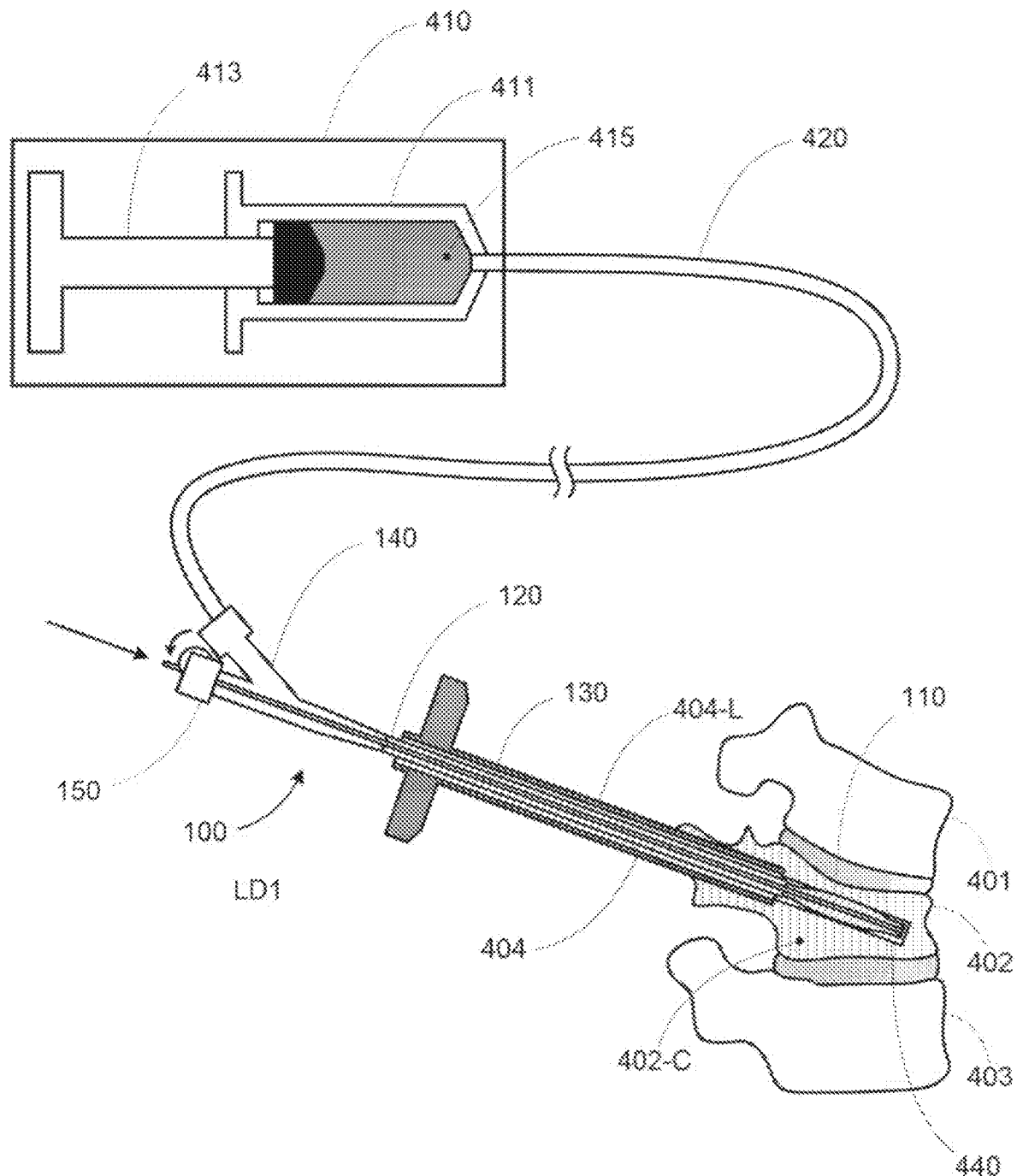

Then, as shown in FIG. 4D. inflatable structure 110 can be extended from within shaft 120 by advancing inner shaft 130 relative to shaft 120 (e.g., by actuating retraction controller 150 or by directly manipulating shaft 130). Note that in various other embodiments, inflatable bone tamp 100 can be inserted into vertebra 402 with inflatable structure 110 already partially or fully extended.

Note further that for exemplary purposes, inflatable structure 110 is extended into a pre-existing channel 440 within cancellous bone 402-C. In various embodiments, channel 440 can be created prior to placement of inflatable bone tamp 100 through cannula 404 (e.g., using a drill, rod, needle, obturator, rasp, or any other instrument). In various other embodiments, inflatable bone tamp 100 can create its own path as it is moved through cancellous bone 402-C (e.g., using a sharpened tip, drill, cone, or other boring feature at the end of inflatable structure 110 or inner shaft 130).

As further shown in FIG. 4D, inflatable bone tamp 100 is also coupled to inflation mechanism 410 by a flow channel 420 (e.g., flexible tubing) either before or after insertion of inflatable bone tamp 100 into cannula 404. For exemplary purposes, inflation mechanism 410 is depicted as a syringe having a plunger 413 for expressing inflation fluid 415 (e.g., saline solution, air, contrast solution, or any other fluid) from a barrel 411. Note that in various other embodiments, inflation mechanism 410 can be any system for delivering inflation, such as a syringe, pump, or compressed gas system, among others. Furthermore, in various other embodiments, inflation mechanism 410 can be directly connected to connector 140.

Shafts 120 and 130 are used to position inflatable structure 110 at a desired location within cancellous bone 402-C. As noted above with respect to FIGS. 1A-1B, in some embodiments, inflatable bone tamp 100 can include one or more radiopaque markers, markings, or materials to facilitate this placement under remote visualization (e.g., fluoroscopic visualization).

Figure 4E:
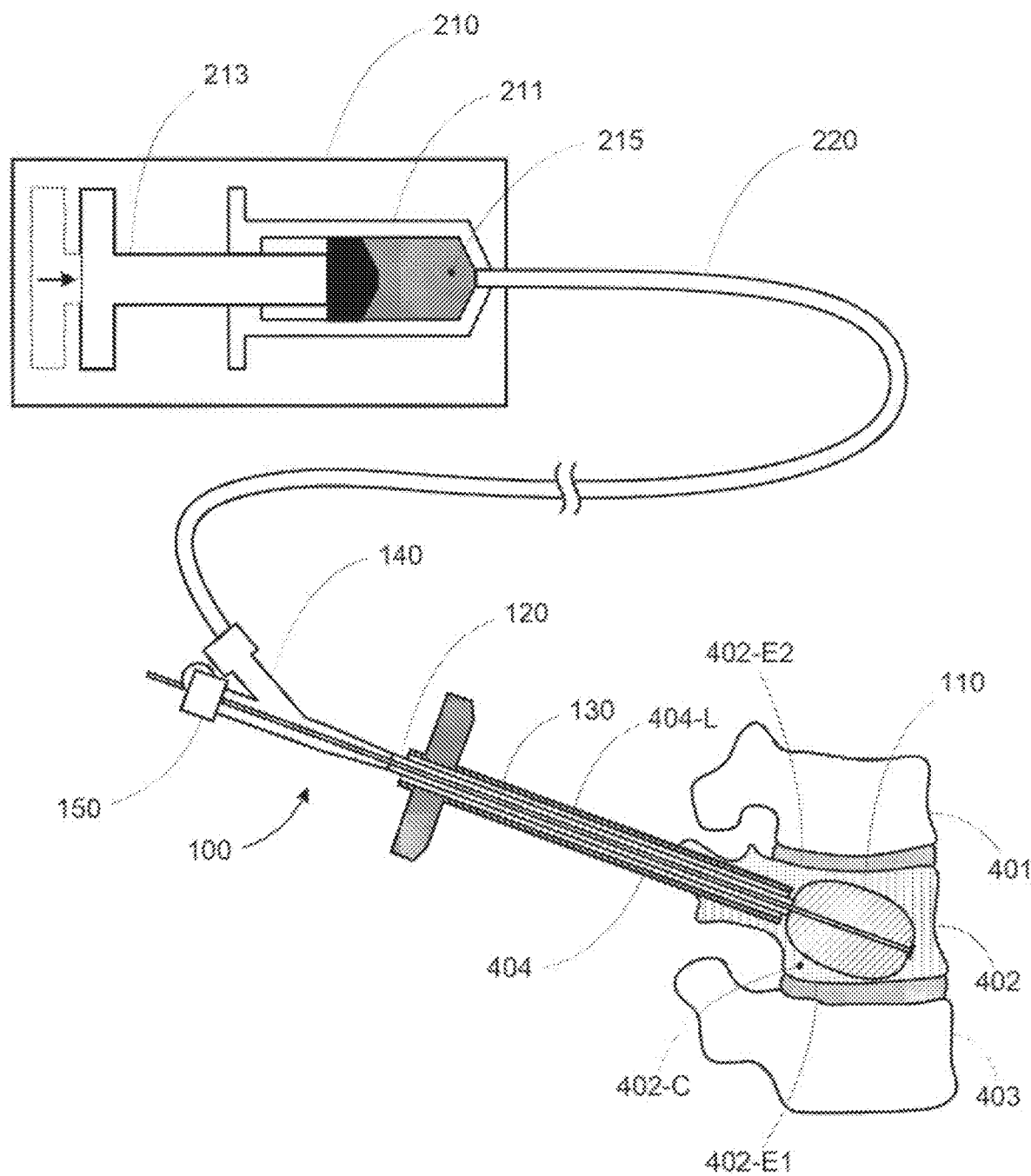

Next, as shown in FIG. 4E, inflation mechanism 410 is actuated to drive inflation fluid 415 into inflatable structure 110, and inflatable structure 110 expands within fractured vertebra 402. For example, in the embodiment shown in FIG. 4E, a force is applied to drive plunger 413 through barrel 411, thereby expressing inflation fluid 415 through flow channel 420, connector 140, shaft 120, and into inflatable structure 110. The resulting expansion of inflatable structure 110 compresses the surrounding cancellous bone 402-C to create a cavity within vertebra 402.

In addition, as inflatable structure 110 performs this compression of cancellous bone 402-C, it approaches the harder endplates 402-E1 (inferior) and 402-E2 (superior) of vertebra 402. In many instances, the continued expansion of inflatable structure 110 can move endplates 402-E1 and 402-E2 apart, thereby providing beneficial height restoration of fractured vertebra 402.

Figure 4F:
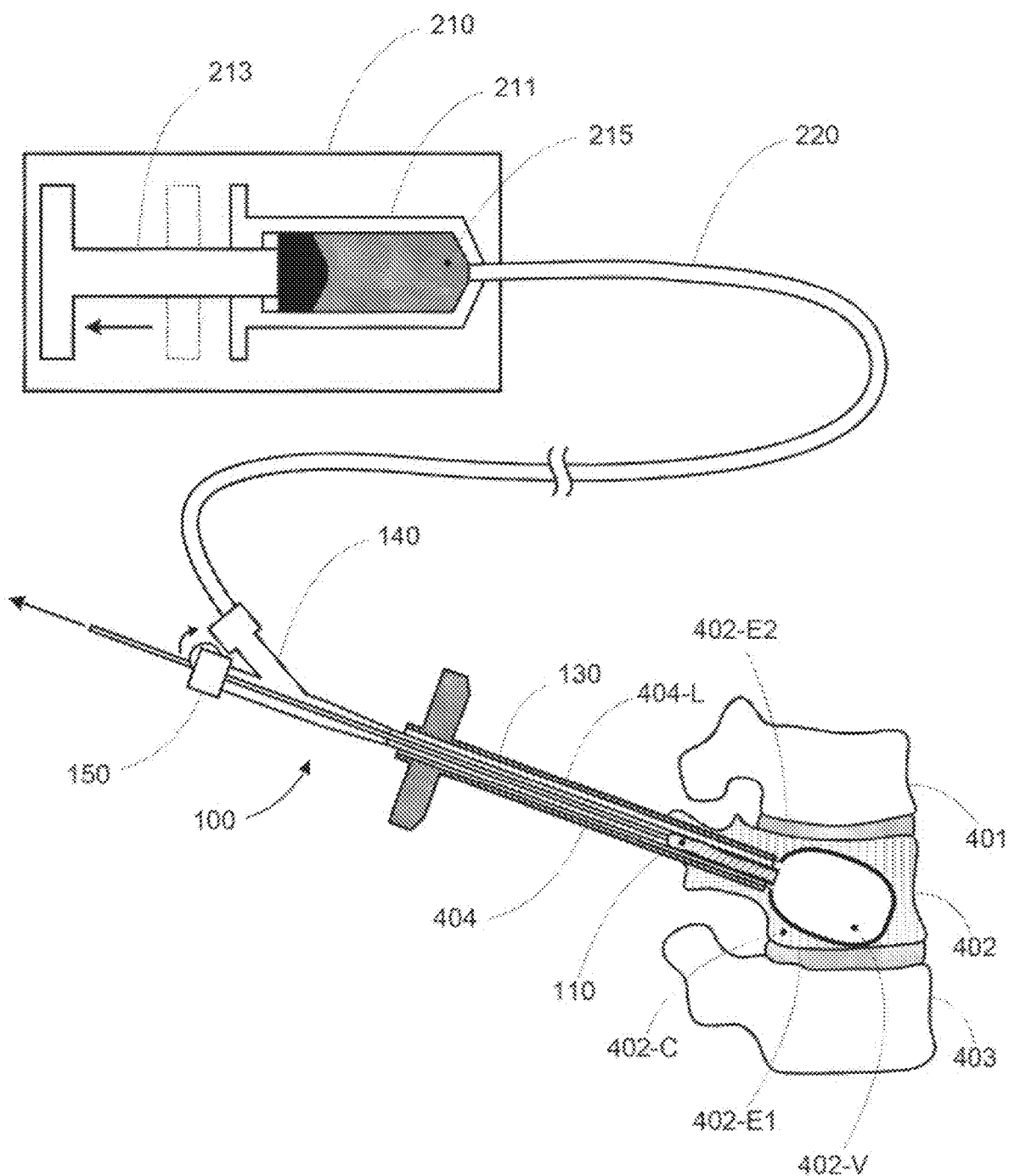

Once inflatable structure 110 has been expanded to a desired volume and/or a desired height restoration has been achieved in vertebra 402, inflatable structure 110 is deflated, as shown in FIG. 4F. Inner shaft 130 can then be used to retract inflatable structure 110 (e.g., via direct manipulation or via control by retraction controller 150) into outer shaft 120 to facilitate removal of inflatable bone tamp 100 from cannula 404. This retraction can beneficially minimize the risk of inflatable structure 110 becoming snagged on the distal edge of cannula 404 during withdrawal.

Note also that in the event of a radial tear of inflatable structure 110, inner shaft 130 can pull the separated proximal portion of inflatable structure 110 into shaft 120 prior to removal of inflatable bone tamp 100 from cannula 404. This can minimize the chances of any pieces of inflatable structure 110 remaining within the patient upon removal of inflatable bone tamp 100 through lumen 404-L of cannula 404.

Figure 4G:
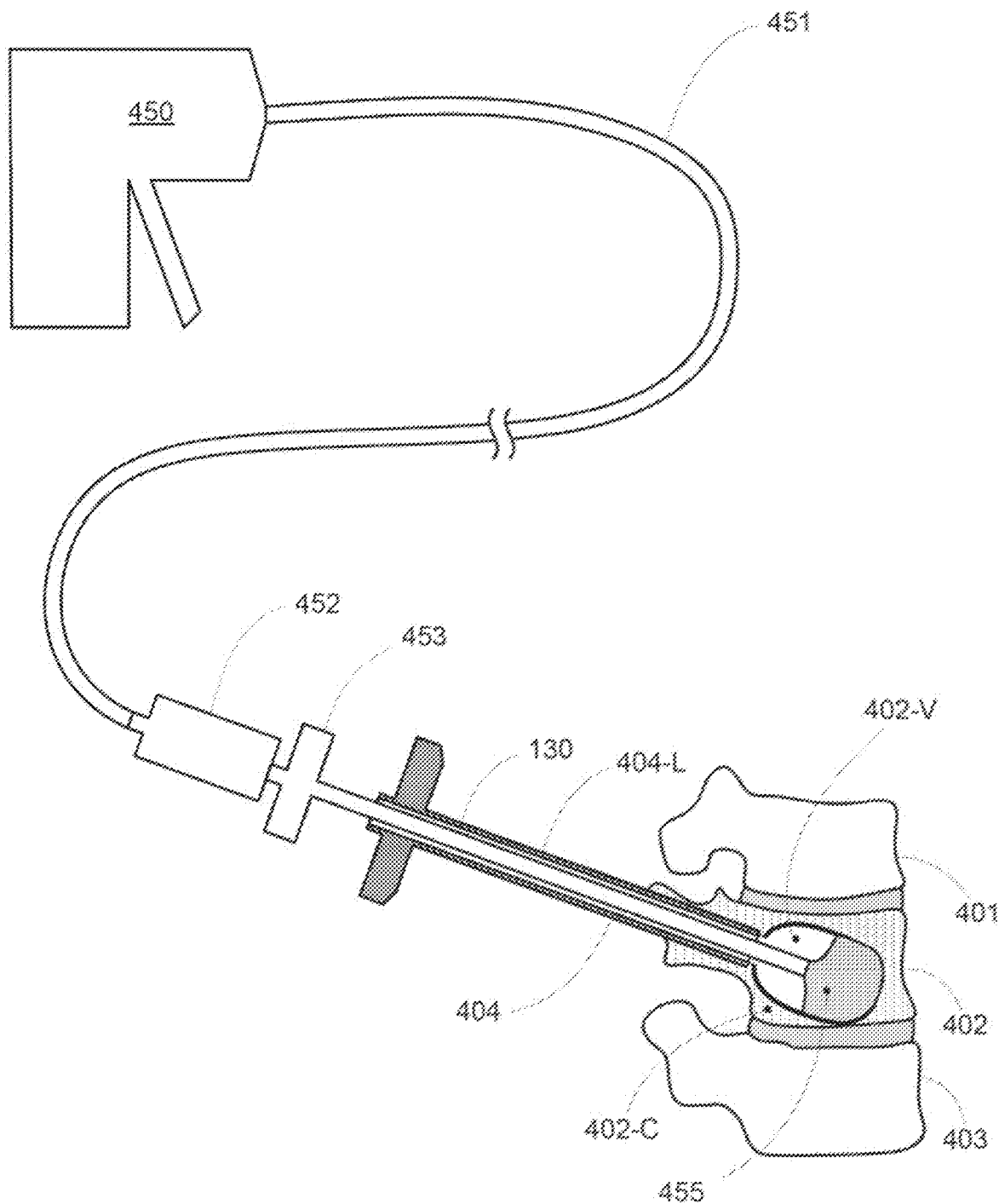

As shown further in FIG. 4F, the result of the previously described expansion procedure is a well-defined cavity 402-V in cancellous bone 402-C, and a restoration of some or all of the original height of vertebra 402. Cavity 402-V can then be filled with bone filler material 255 (e.g., PMMA), as shown in FIG. 4G. A delivery nozzle 453 can be inserted through cannula 404 and into cavity 402-V, and can then be used to direct bone filler material 455 into cavity 402-V.

As shown in FIG. 4G, in one embodiment, a quantity of bone filler material 455 can be housed in a cartridge 452 attached to delivery nozzle 453. A hydraulic actuator 450 can then be used to remotely express bone filler material 455 from cartridge 452 via a hydraulic line 451 (e.g., cartridge 452 can include a piston that is driven by the hydraulic pressure supplied by hydraulic line 451). Note, however, that in various other embodiments, bone filler material 455 can be delivered to cavity 402-V in any number of different ways (e.g., a high pressure cement delivery pump that delivers the cement to nozzle 453 through a flexible line, or a syringe or other delivery device filled with bone filler material 455 that is attached directly to nozzle 453), In addition, in various other embodiments, bone filler material 455 can be delivered in multiple portions of the same or different materials (e.g., a bone cement followed by a biologic agent).

Figure 4H:
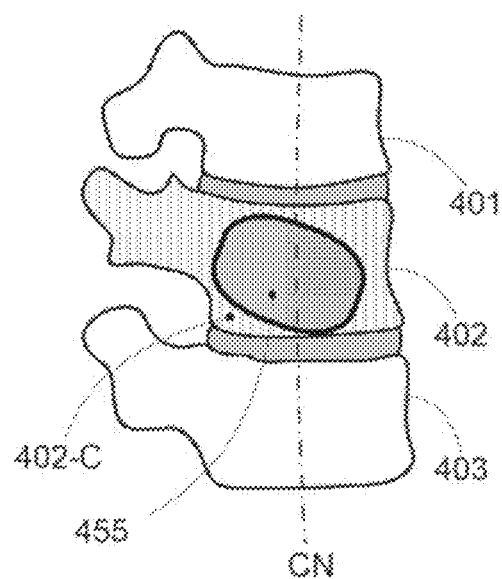

Once the filling operation is complete, delivery nozzle 453 and cannula 404 are removed from vertebra 402 (and the patients body) as shown in FIG. 4H. Upon hardening, bone filler material 455 provides structural support for vertebra 402, thereby substantially restoring the structural integrity of the bone and the proper musculoskeletal alignment of the spine. As shown in FIG. 4H, due to the restoration of height in fractured vertebra 402, the abnormal curvature CK shown in FIG. 4A is corrected to a normal curvature CN. In this manner, the pain and attendant side effects of a vertebral compression fracture can be addressed by a minimally invasive kyphoplasty procedure.

Note that although a kyphoplasty procedure is depicted and described for exemplary purposes, inflatable bone tamp 100 can be similarly used in any other target surgical location in or around bone, such as a tibial plateau fracture, a proximal humerus fracture, a distal radius fracture, a calcaneus fracture, a femoral head fracture, among others. In fact, the ability to effectively "sheath" inflatable structure 110 and/or recover from radial tears using shafts 120 and 130 may be even more beneficial when inflatable bone tamp 100 is used in potentially more severe fracture environments such as might be present for those long bone fractures mentioned above. Various other usages will be readily apparent.

Figure 5:
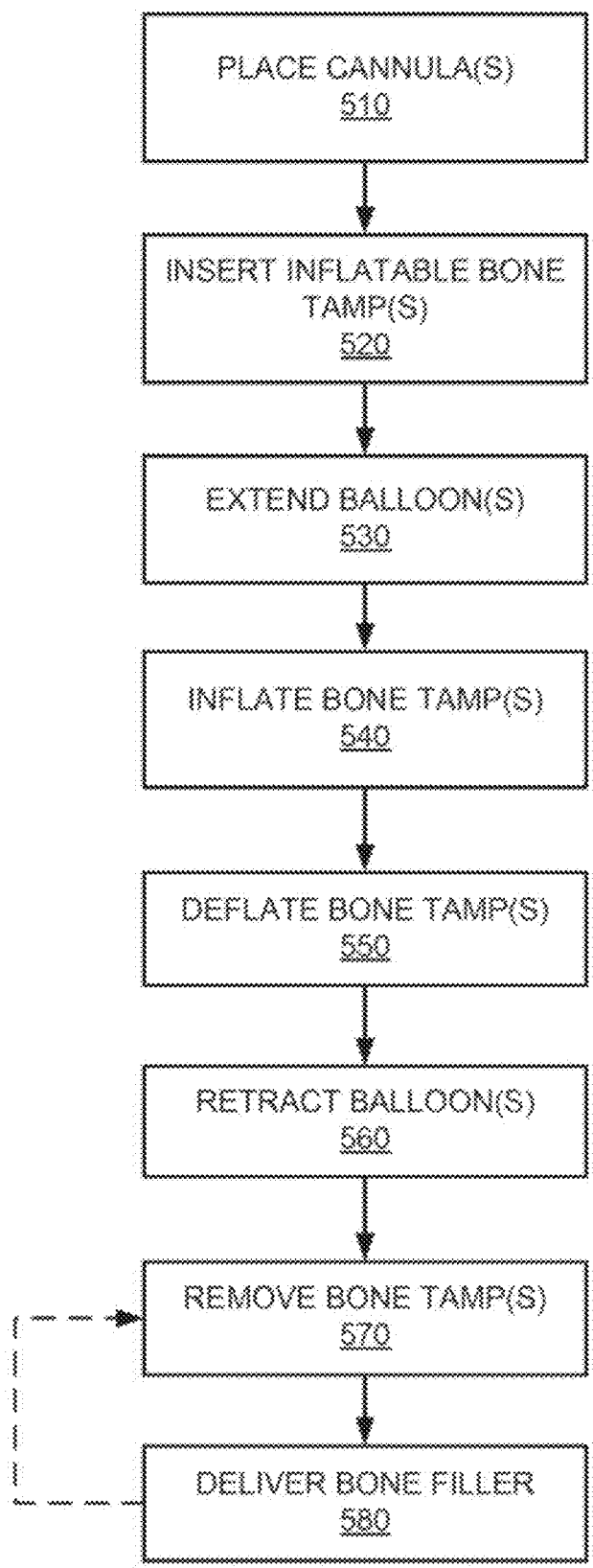
FIG. 5 shows a flow diagram for an exemplary surgical procedure using the inflatable bone tamp of FIGS. 1A-1B.

FIG. 5 shows a flow diagram of a process for performing a surgical procedure such as kyphoplasty using an inflatable bone tamp incorporating a shaft having a reduced diameter region. In a PLACE CANNULA(S) step 510, a cannula is positioned within a patient to provide a path to a target surgical location (e.g., as described with respect to FIG. 4B). Note that although a unilateral procedure is described above for clarity, in various other embodiments, a bilateral procedure can be used (e.g., placing two cannulas to provide access through both pedicles of a vertebra).

Then, in an INSERT INFLATABLE BONE TAMP(S) step 520, an inflatable bone tamp having a retractable inflatable structure (e.g., as described with respect to FIGS. 1A-1B) is placed within the patient through the cannula (e.g., as described with respect to FIG. 3C). Note once again that if multiple cannulas have been placed in step 410, an inflatable bone tamp can be inserted into each cannula (with at least one of the inflatable bone tamps exhibiting a shaft having a reduced diameter region for the inflatable structure).

In an optional EXTEND BALLOON(S) step 530, if not already extended, the inflatable structure(s) of the positioned inflatable bone tamp(s) can be extended (e.g., as described with respect to FIG. 4D. Next, in an INFLATE BONE TAMP(S) step 540, the inflatable bone tamp(s) is (are) inflated to create a cavity(ies) in cancellous bone and, ideally, at least partially restore the original cortical bone profile (e.g., as described with respect to FIG. 4E). Note that if multiple inflatable bone tamps have been introduced in step 520, their inflation can be sequential, simultaneous, sequentially incremental (e.g., partially inflating one before partially or fully inflating another), or any other order.

The inflatable bone tamp(s) is (are) then deflated in a DEFLATE BONE TAMP(S) step 550 (e.g., as described with respect to FIG. 4F), the inflatable structure(s) is (are) optionally retracted in a RETRACT BALLOON(S) step 560 (e.g., as further described with respect to FIG. 4F, and the inflatable bone tamp(s) is (are) withdrawn from the patient in a REMOVE BONE TAMP(S) step 570 (e.g., as described with respect to FIG. 4F).

Next, in a DELIVER BONE FILLER step 580, a bone filler material (e.g., bone cement) is conveyed to the cavity formed by the inflatable bone tamp to create a permanent reinforcing structure within the bone (e.g., as described with respect to FIGS. 4G and 4H). Note that if multiple bone tamps have been placed within the patient (e.g., in a bilateral procedure) in step 520, one or more of those inflatable bone tamps can be left (inflated) within the patient to provide support for the bone structure during subsequent material delivery during step 580. The process can then loop back to step 570 and then step 580 until all inflatable bone tamps have been removed, and all the resulting cavities in the bone have been filled with bone filler material.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A device for performing a surgical procedure, the device comprising:
    an outer shaft defining an interior lumen;
    an inflatable structure coupled to a distal end the outer shaft;
    a connector fixed to a proximal end of the outer shaft, the connector defining a cavity in communication with the interior lumen and a port in communication with the cavity;
    an inner shaft disposed within the cavity and the interior lumen, wherein the inner shaft is movable with respect to the outer shaft to retract the inflatable structure into the interior lumen and to extend the inflatable structure outside of the interior lumen, a distal end of the inner shaft being closed, the device having a maximum length defined by a distance from a proximal end of the inner shaft to the distal end of the inner shaft; and
    a retraction controller comprising a housing that is fixed to the connector, the retraction controller comprising rotary driver elements having the inner shaft positioned therebetween such that the inner shaft spaces outer surfaces of the rotary driver elements apart from one another as the rotary driver elements rotate, the rotary driver elements being positioned in the housing and configured to move the inner shaft relative to the outer shaft in opposite first and second directions to secure a relative position between the inner shaft and the outer shaft, the reaction controller comprising a lock configured to fix the relative position between the inner shaft and the outer shaft when the inner shaft is fully extended and fully retracted relative to the outer shaft, the distal end of the inner shaft being positioned entirely within the interior lumen when the inner shaft is fully retracted, the housing including a proximal wall and a passageway extending through the proximal wall, the inner shaft extending through the passageway, the proximal end of the inner shaft comprising a stop having a diameter larger than a diameter of the passageway to limit extension of the inner shaft relative to the outer shaft,
    wherein the retraction controller is configured to itself rotate to rotate the inner shaft such that the inflatable structure wraps around the inner shaft.

2. A device as recited in claim 1, wherein the inner shaft is rigid.

3. A device as recited in claim 1, wherein a distal end of the inflatable structure is permanently fixed with the distal end of the inner shaft such that the distal end of the inner shaft protrudes beyond the distal end of the inflatable structure and the inflatable structure forms a single inflated portion.

4. A device as recited in claim 1, wherein the rotary driver elements are entirely spaced apart from one another when the inner shaft is positioned therebetween.

5. A device as recited in claim 1, wherein the rotary driver elements are gears having teeth and the inner shaft comprises a series of notches that engage with the teeth so as to space the teeth apart from one another as the rotary driver elements rotate.

6. A device as recited in claim 1, wherein the lock comprises a releasable latch.

7. A device as recited in claim 1, wherein:
a proximal end of the inflatable structure is coupled to the distal end of the outer shaft, and
a distal end of the inflatable structure is coupled to the distal end of the inner shaft.

8. A device as recited in claim 7, wherein the distal end of the inner shaft comprises a shoulder having an increased-diameter positioned distal to the distal end of the inflatable structure.

9. The device of claim 1, wherein the rotary driver elements are each configured to rotate in response to an actuator positioned within the housing.

10. The device of claim 1, wherein the inner shaft defines an inflation lumen that terminates at the distal end of the inner shaft.

11. A device as recited in claim 1, wherein the retraction controller is spaced apart from the outer shaft by the connector.

12. A device as recited in claim 1, wherein the housing includes an inner surface defining an aperture and an opposite outer surface, a first portion of each of the rotary driver elements being positioned in the aperture and a second portion of each of the rotary driver elements extending through the outer surface.

13. A device as recited in claim 1, wherein the housing includes an inner surface defining an aperture, a portion of each of the rotary driver elements being positioned in the aperture and a lever of one of the rotary driver elements being positioned outside of the aperture.

14. A device as recited in claim 1, wherein the inner shaft is non-cannulated.

15. A device as recited in claim 1, wherein the cavity extends parallel to a longitudinal axis defined by the outer shaft, the port extending transverse to the cavity.

16. A device for performing a surgical procedure, the device comprising:
an outer shaft defining an interior lumen;
an inflatable structure coupled to a distal end of the outer shaft;
a connector fixed to a proximal end of the outer shaft, the connector defining a cavity in communication with the interior lumen and a port in communication with the cavity;
an inner shaft at least partially disposed within the cavity and the interior lumen, wherein the inner shaft is movable with respect to the outer shaft to retract the inflatable structure into the interior lumen and to extend the inflatable structure outside of the interior lumen, a distal end of the inner shaft being closed, the device having a maximum length defined by a distance from a proximal end of the inner shaft to the distal end of the inner shaft; and
a retraction controller comprising a housing that is fixed to the connector such that the housing is spaced apart from the outer shaft by the connector, the retraction controller comprising rotary driver elements having the inner shaft positioned therebetween such that the inner shaft spaces teeth of one of the rotary driver elements apart from teeth of another one of the rotary driver elements as the rotary driver elements rotate, the rotary driver elements being positioned within the housing and configured to move the inner shaft relative to the outer shaft in opposite first and second directions to secure a relative position between the inner shaft and the outer shaft, the reaction controller comprising a lock configured to fix the relative position between the inner shaft and the outer shaft when the inner shaft is fully extended and fully retracted relative to the outer shaft, the distal end of the inner shaft being positioned entirely within the interior lumen when the inner shaft is fully retracted, the housing including a proximal wall and a passageway extending through the proximal wall, the inner shaft extending through the passageway, the proximal end of the inner shaft comprising a stop having a diameter larger than a diameter of the passageway to limit extension of the inner shaft relative to the outer shaft,
wherein the retraction controller is configured to itself rotate to rotate the inner shaft such that the inflatable structure wraps around the inner shaft.

17. A device as recited in claim 16, wherein a distal end of the inflatable structure is permanently fixed with the distal end of the outer shaft and the distal end of the inner shaft such that the distal end of the inner shaft protrudes beyond the distal end of the inflatable structure and the inflatable structure forms a single inflated portion.

18. A device as recited in claim 16, wherein the inner shaft defines an inflation lumen that terminates at the distal end of the inner shaft.

19. A device for performing a surgical procedure, the device comprising:
an outer shaft defining an interior lumen;
an inflatable structure coupled to a distal end of the outer shaft;
a connector fixed to a proximal end of the outer shaft, the connector defining a cavity in communication with the interior lumen and a port in communication with the cavity;
an inner shaft at least partially disposed within the cavity and the interior lumen, wherein the inner shaft is movable with respect to the outer shaft to retract the inflatable structure into the interior lumen and to extend the inflatable structure outside of the interior lumen, a distal end of the inner shaft being closed, the device having a maximum length defined by a distance from a proximal end of the inner shaft to the distal end of the inner shaft; and
a retraction controller comprising a housing that is fixed to the connector such that the housing is spaced apart from the outer shaft by the connector, the retraction controller comprising rotary driver elements having the inner shaft positioned therebetween such that teeth of the rotary driver elements are disposed within notches of the inner shaft and the inner shaft spaces the teeth of one of the rotary driver elements apart from the teeth of another one of the rotatory driver elements as the rotary driver elements rotate, the rotary driver elements being positioned within the housing and configured to move the inner shaft relative to the outer shaft in opposite first and second directions to secure a relative position between the inner shaft and the outer shaft, the reaction controller comprising a lock configured to fix the relative position between the inner shaft and the outer shaft when the inner shaft is fully extended and fully retracted relative to the outer shaft, the distal end of the inner shaft being positioned entirely within the interior lumen when the inner shaft is fully retracted, the housing including a proximal wall and a passageway extending through the proximal wall, the inner shaft extending through the passageway, the proximal end of the inner shaft comprising a stop having a diameter larger than a diameter of the passageway to limit extension of the inner shaft relative to the outer shaft, wherein the retraction controller is configured to itself rotate to rotate the inner shaft such that the inflatable structure wraps around the inner shaft.

* * * * *